United States Patent [19]

Haug et al.

[11] Patent Number: 4,994,601
[45] Date of Patent: Feb. 19, 1991

[54] HERBICIDAL α-(5-ARYLOXY-NAPHTHALEN-1-YL-OXY)-PROPIONIC ACID DERIVATIVES

[75] Inventors: Michael Haug, Bergisch Gladbach; Hans-Joachim Santel, Leverkusen; Robert R. Schmidt, Bergisch Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 247,817

[22] Filed: Sep. 22, 1988

[30] Foreign Application Priority Data

Sep. 30, 1987 [DE] Fed. Rep. of Germany ....... 3733067

[51] Int. Cl.$^5$ .............................................. C07C 69/76
[52] U.S. Cl. ..................... 560/56; 568/586; 568/609; 568/610; 568/632; 568/633; 71/108; 71/124
[58] Field of Search .................. 560/56; 568/586, 609, 568/610, 632, 633; 71/108, 124

[56] References Cited

FOREIGN PATENT DOCUMENTS 179015  4/1986  European Pat. Off. .
3434447 3/1986  Fed. Rep. of Germany .
165346  7/1986  Japan .
10041   1/1987  Japan .

OTHER PUBLICATIONS

JP 79/32477, vol. 79, No. 42, Polymer Chemistry—p. 5-p. 6.
106424j, Sataka et al., "Thermal Recording Materials", Chem. Ab., V. 107, Sep. 1987, pp. 1-2.

Primary Examiner—Paul J. Killos
Attorney, Agent, or Firm—Sprung Horn Kramer & Woods

[57] ABSTRACT

Herbicidal α-(5-aryloxy-naphthalen-1-yl-oxy)-propionic acid derivatives of the formula

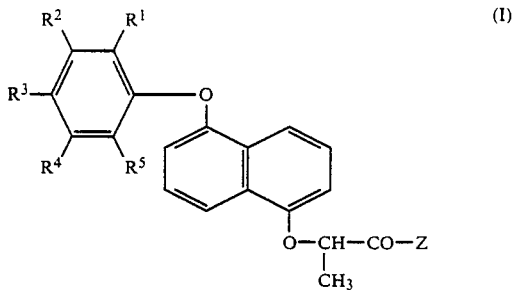

in which
$R^1$ stands for hydrogen, halogen, cyano or trifluoromethyl,
$R^2$ stands for hydrogen or halogen,
$R^3$ stands for halogen, cyano, trifluoromethyl or trifluoromethoxy,
$R^4$ stands for hydrogen or halogen,
$R^5$ stands for hydrogen or halogen and
Z stands for halogen, hydroxyl, amino, alkylamino, alkenylamino, alkinylamino, arylamino, aralkylamino, alkoxycarbonylalkylamino, cyanamino, dialkylamino, dialkenylamino, alkylsulphonylamino, arylsulphonylamino, hydroxylamino, alkoxyamino, hydrazino, alkylsulphonylhydrazino, arylsulphonylhydrazino, alkylthio, arylthio, aralkylthio, alkoxycarbonylalkylthio or for the —O—$R^6$ group, wherein $R^6$ can be various organic radicals.

The starting material naphthol of the formula

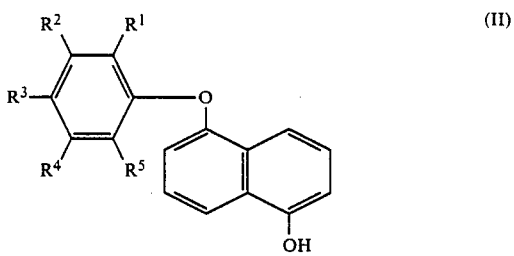

is also new.

11 Claims, No Drawings

HERBICIDAL α-(5-ARYLOXY-NAPHTHALEN-1-YL-OXY)-PROPIONIC ACID DERIVATIVES

The invention relates to new α-(5-aryloxy-naphthalen-1-yl-oxy)-propionic acid derivatives, processes and new intermediates for their preparation and their use as herbicides.

It has already been disclosed that certain 7-aryloxy-naphthalen-2-yl-oxy-carboxylic acid derivatives, such as, for example, ethyl α-(7-(2-chloro-4-trifluoromethylphenoxy)-naphthalen-2-yl-oxy)-propionate, are herbicidally active (compare EP-A 179,015). The action of these known compounds against weeds and their tolerability by cultivated plants are, however, not always satisfactory.

New α-(5-aryloxy-naphthalen-1-yl-oxy)-propionic acid derivatives of the general formula (I)

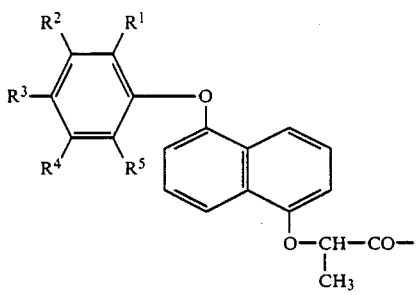

in which
  $R^1$ stands for hydrogen, halogen, cyano or trifluoromethyl,
  $R^2$ stands for hydrogen or halogen,
  $R^3$ stands for halogen, cyano, trifluoromethyl or trifluoromethoxy,
  $R^4$ stands for hydrogen or halogen,
  $R^5$ stands for hydrogen or halogen and
  Z stands for halogen, hydroxyl, amino, alkylamino, alkenylamino, alkinylamino, arylamino, aralkylamino, alkoxycarbonylalkylamino, cyanamino, dialkylamino, dialkenylamino, alkylsulphonylamino, arylsulphonylamino, hydroxylamino, alkoxyamino, hydrazino, alkylsulphonylhydrazino, arylsulphonylhydrazino, alkylthio, arylthio, aralkylthio, alkoxycarbonylalkylthio or for the —O—$R^6$ group,
wherein
  $R^6$ stands for an optionally halogen-substituted radical from the series comprising alkyl, alkenyl, alkinyl, alkoxyalkyl, alkylthioalkyl, alkylsulphinylalkyl, alkylsulphonylalkyl, aryloxyalkyl, trialkylsilylalkyl, arylthioalkyl, aralkoxyalkyl, aralkylthioalkyl, alkoxycarbonylalkyl, alkylaminocarbonylalkyl, aralkyl, azolylalkyl, alkylideneamino or for an ammonium equivalent, an alkylammonium equivalent, an alkali metal equivalent or an alkaline earth metal equivalent or for the group

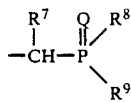

wherein $R^7$ stands for hydrogen, alkyl, aryl, furyl, thienyl or pyridyl,
  $R^8$ stands for alkyl or alkoxy,
  $R^9$ stands for alkoxy and
  Q stands for oxygen or sulphur, or
  $R^6$ stands for the —$(CH_2)_n$—$R^{10}$ group,
wherein
  $R^{10}$ stands for a heterocyclic radical from the series comprising furyl, tetrahydrofuryl, oxotetrahydrofuryl, thienyl, tetrahydrothienyl, perhydropyranyl, oxazolyl, thiazolyl, thiadiazolyl, dioxolanyl, perhydropyrrolyl, oxoperhydropyrrolyl, pyridinyl or pyrimidinyl, each of which is optionally substituted by halogen and/or alkyl, and n stands for the numbers 0, 1 or 2,
have now been found.

The compounds of the formula (I) contain at least one asymmetrically substituted carbon atom and can therefore exist in different enantiomeric forms. The invention relates both to the possible individual isomers and to the mixtures of these isomers.

It has further been found that the new α-(5-aryloxynaphthalen-1-yl-oxy)-propionic acid derivatives of the formula (I) are obtained when (a) 5-aryloxy-1-naphthols of the general formula (II)

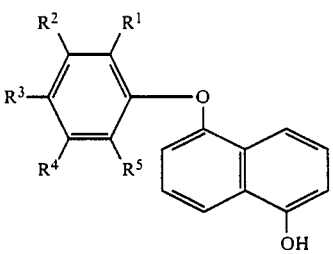

in which
  $R^1$, $R^2$, $R^3$, $R^4$ and $R^5$ have the abovementioned meanings,
are reacted with propionic acid derivatives of the general formula (III)

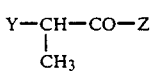

in which
  Z has the abovementioned meaning and
  Y stands for a nucleophilic leaving group, if appropriate in the presence of an acid acceptor and if appropriate in the presence of a diluent, or (b) halogeno-benzene derivatives of the general formula (IV)

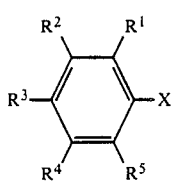

in which
  $R^1$, $R^2$, $R^3$, $R^4$ and $R^5$ have the abovementioned meanings and
  X stands for halogen, are reacted with α-(5-hydroxy-naphthalen-1-yl-oxy)-propionic acid derivatives of the general formula (V)

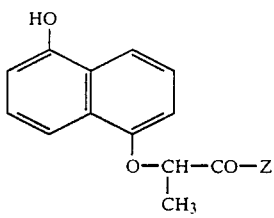

in which

Z has the abovementioned meaning,
if appropriate in the presence of an acid acceptor and if appropriate in the presence of a diluent, or (c) for the case in which Z stands for hydroxyl and the radicals $R^1$ to $R^5$ have the abovementioned meanings, when compounds of the general formula (I) in which Z stands for methoxy or ethoxy, and the radicals $R^1$ to $R^5$ have the abovementioned meanings, are reacted with an alkali metal hydroxide in the presence of water and if appropriate in the presence of an organic solvent and are then acidified—if appropriate after concentration—using a mineral acid, or (d) for the case in which Z stands for halogen and the radicals $R^1$ to $R^5$ have the abovementioned meanings, when compounds of the general formula (I) in which Z stands for hydroxyl and the radicals $R^1$ to $R^5$ have the above-mentioned meanings, are reacted with a halogenating agent, if appropriate in the presence of a catalyst and if appropriate in the presence of a diluent, or (e) for the case in which Z, with the exception of halogen, has the abovementioned meaning and the radicals $R^1$ to $R^5$ have the abovementioned meanings, when compounds of the general formula (I) in which Z stands for halogen and the radicals $R^1$ to $R^5$ have the abovementioned meanings, are reacted with compounds of the general formula (VI)

$$H-Z \quad (VI)$$

in which

Z, with the exception of halogen, has the abovementioned meaning,
if appropriate in the presence of an acid acceptor and if appropriate in the presence of a diluent, or (f) for the case in which Z stands for the —O—$R^6$ group, wherein $R^6$, with the exception of ammonium, alkylammonium, alkali metal and alkaline earth metal, has the abovementioned meaning and the radicals $R^1$ to $R^5$ have the abovementioned meanings, when compounds of the general formula (I) in which Z stands for hydroxyl and the radicals $R^1$ to $R^5$ have the abovementioned meanings, are reacted with compounds of the general formula (VII)

$$X^1-R^6 \quad (VII)$$

in which $R^6$, with the exception of ammonium, alkylammonium, alkali metal and alkaline earth metal, has the abovementioned meanings and
$X^1$ stands for halogen,
if appropriate in the presence of an acid acceptor and if appropriate in the presence of a diluent.

Finally, it has been found that the new α-(5-aryloxy)-naphthalen-1-yl-oxy)-propionic acid derivatives of the general formula (I) exhibit strong herbicidal properties.

Surprisingly, the α-(5-aryloxy-naphthalen-1-yl-oxy)-propionic acid derivatives of the formula (I) according to the invention show, together with good tolerability in important cultivated plants, substantially stronger action against certain problem weeds, such as in particular millet species than ethyl α-(7-(2-chloro-4-trifluoromethylphenoxy)-naphthalen-2-yl-oxy)-propionate, which is a structurally similar previously known active compound with an equivalent type of action.

The invention preferably relates to compounds of the formula (I) in which $R^1$ stands for hydrogen, fluorine, chlorine, bromine, cyano or trifluoromethyl, $R^2$ stands for hydrogen, fluorine or chlorine, $R^3$ stands for fluorine, chlorine, bromine, cyano, trifluoromethyl or trifluoromethoxy, $R^4$ stands for hydrogen, fluorine or chlorine, $R^5$ stands for hydrogen, fluorine, chlorine or bromine and Z stands for chlorine, hydroxyl, amino, $C_1$-$C_6$-alkylamino, $C_3$-$C_4$-alkenylamino, $C_3$-$C_4$-alkinylamino, phenylamino, benzylamino, $C_1$-$C_4$-alkoxycarbonyl-$C_1$-$C_2$-alkylamino, cyanamino, di-($C_1$-$C_4$-alkyl)-amino, di-($C_3$-$C_4$-alkenyl)-amino, $C_1$-$C_4$-alkylsulphonylamino, phenylsulphonylamino, tolylsulphonylamino, hydroxylamino, $C_1$-$C_6$-alkoxyamino, hydrazino, $C_1$-$C_4$-alkylsulphonylhydrazino, phenylsulphonylhydrazino, tolylsulphonylhydrazino, $C_1$-$C_4$-alkylthio, phenylthio, benzylthio, $C_1$-$C_4$-alkoxycarbonyl-$C_1$-$C_2$-alkylthio or for the —O—$R^6$ group, wherein $R^6$ stands for a radical from the series comprising $C_1$-$C_6$-alkyl, $C_3$-$C_4$-alkenyl, $C_3$-$C_4$-alkinyl, $C_1$-$C_4$-alkoxy-$C_1$-$C_4$-alkyl, $C_1$-$C_4$-alkylthio-$C_1$-$C_4$-alkyl, $C_1$-$C_4$-alkylsulphinyl-$C_1$-$C_4$ alkyl, $C_1$-$C_4$-alkylsulphonyl-$C_1$-$C_4$-alkyl, phenoxy-$C_1$-$C_3$-alkyl, trimethylsilylmethyl, phenylthio-$C_1$-$C_3$-alkyl, benzyloxy-$C_1$-$C_3$-alkyl, benzylthio-$C_1$-$C_3$-alkyl, $C_1$-$C_4$-alkoxy-carbonyl-$C_1$-$C_2$-alkyl, $C_1$-$C_4$-alkylamino-carbonyl-$C_1$-$C_2$-alkyl, benzyl, pyrazolyl-$C_1$-$C_4$-alkyl or $C_2$-$C_4$-alkylideneamino, each of which is optionally substituted by fluorine and/or chlorine, or for an ammonium equivalent, a $C_1$-$C_4$-alkylammonium equivalent, or a sodium equivalent potassium equivalent or calcium equivalent, or for the group

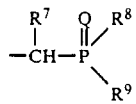

wherein $R^7$ stands for hydrogen, $C_1$-$C_4$-alkyl, phenyl, furyl, thienyl or pyridyl, $R^8$ stands for $C_1$-$C_4$-alkyl or $C_1$-$C_4$-alkoxy, $R^9$ stands for $C_1$-$C_4$-alkoxy and Q stands for oxygen or sulphur, or $R^6$ stands for the —$(CH_2)_n$—$R^{10}$ group, wherein n stands for the numbers 0, 1 or 2 and $R^{10}$ stands for a heterocyclic radical from the series comprising furyl, tetrahydrofuryl, oxotetrahydrofuryl, thienyl, tetrahydrothienyl, perhydropyranyl, oxazolyl, thiazolyl, thiadiazolyl, dioxolanyl, perhydropyrrolyl, oxoperhydropyrrolyl, pyridinyl or pyrimidinyl, each of which is optionally substituted by fluorine, chlorine, bromine and/or $C_1$-$C_4$-alkyl.

The invention relates in particular to compounds of the formula (I) in which $R^1$ stands for hydrogen, cyano, fluorine or chlorine, $R^2$ stands for hydrogen, fluorine or chlorine, $R^3$ stands for trifluoromethyl, $R^4$ stands for hydrogen, fluorine or chlorine, $R^5$ stands for hydrogen, fluorine or chlorine and Z stands for chlorine, hydroxyl, amino, $C_1$-$C_4$-alkylamino, phenylamino, $C_1$-$C_4$-alkoxy-carbonyl-$C_1$-$C_2$-alkylamino, di-($C_1$-$C_3$-alkyl)-amino, $C_1$-$C_4$-alkylsulphonylamino, phenylsulphonylamino, hydroxylamino, cyanamino, $C_1$-$C_4$-alkoxyamino, hydrazino, $C_1$-$C_4$-alkylsulphonylhydrazino, phenylsulphonylhydrazino, $C_1$-$C_4$-alkylthio or $C_1$-$C_4$-alkoxy-carbonyl-$C_1$-$C_2$-alkylthio or for the —O—$R^6$ group, wherein $R^6$ stands for $C_1$-$C_4$-alkyl, $C_1$-$C_2$-alkoxy-$C_1$-$C_2$-alkyl, $C_1$-$C_2$-alkylthio-$C_1$-$C_2$-alkyl, $C_1$-$C_2$-alkylsulphinyl-$C_1$-$C_2$-alkyl, $C_1$-$C_2$-alkylsulphonyl-$C_1$-$C_2$-alkyl, benzyloxy-$C_1$-$C_3$-alkyl, benzylthio-$C_1$-$C_3$-alkyl, $C_1$-$C_4$-alkoxycarbonyl-$C_1$-$C_2$-alkyl, $C_1$-$C_4$-alkylaminocarbonyl-$C_1$-$C_2$-alkyl, benzyl, trimethylsilylmethyl or for an ammonium equivalent, a $C_1$-$C_3$-alkylammonium equivalent, a sodium equivalent, or a potassium equivalent, or for the group

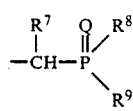

wherein $R^7$ stands for hydrogen, methyl, phenyl, furyl, thienyl or pyridyl, $R^8$ stands for methoxy or ethoxy, $R^9$ stands for methoxy or ethoxy and Q stands for oxygen or sulphur or $R^6$ stands for the (—$CH_2$—)$_n$—$R^{10}$ group, wherein n stands for the numbers 0, 1 or 2 and $R^{10}$ stands for a heterocyclic radical from the series comprising furyl, tetrahydrofuryl, thienyl, perhydropyranyl, oxazolyl, thiazolyl and dioxolanyl, each of which is optionally substituted by chlorine and/or methyl.

The R isomers of the particularly preferred compounds of the formula (I) are very particularly preferred.

If, for example, 5-(4-trifluoromethyl-phenoxy)-1-naphthol and ethyl α-bromo-propionate are used as starting materials for process (a) according to the invention then the course of the reaction can be represented by the following equation:

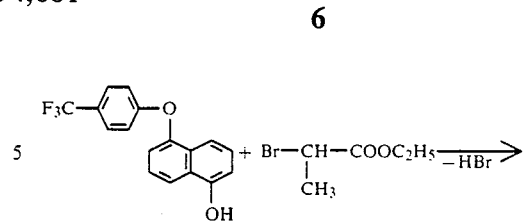

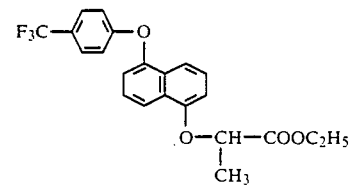

If, for example, 3,4,5-trichloro-benzotrifluoride and propyl α-(5-hydroxy-naphthalen-1-yl-oxy)-propionate are used as starting materials for process (b) according to the invention then the course of the reaction can be represented by the following equation:

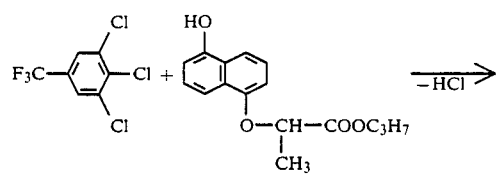

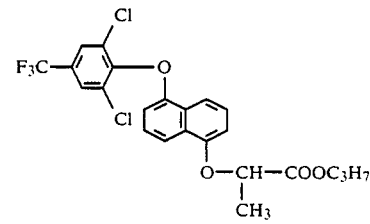

If, for example, methyl α-(5-(2-chloro-4-trifluoromethyl-phenoxy)-naphthalen-1-yl-oxy)-propionate and sodium hydroxide solution are used as starting materials for process (c) according to the invention then the course of the reaction can be represented by the following equation:

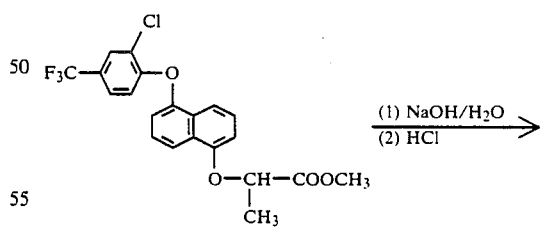

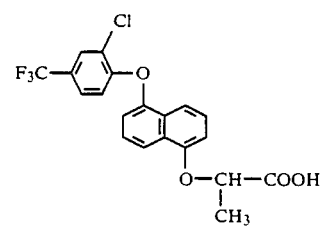

If, for example, α-(5-(2,6-dichloro-3-fluoro-4-trifluoromethyl-phenoxy)-naphthalen-1-yl-oxy)-propionic acid and thionyl chloride are used as starting materials for process (d) according to the invention then the course of the reaction can be represented by the following equation:

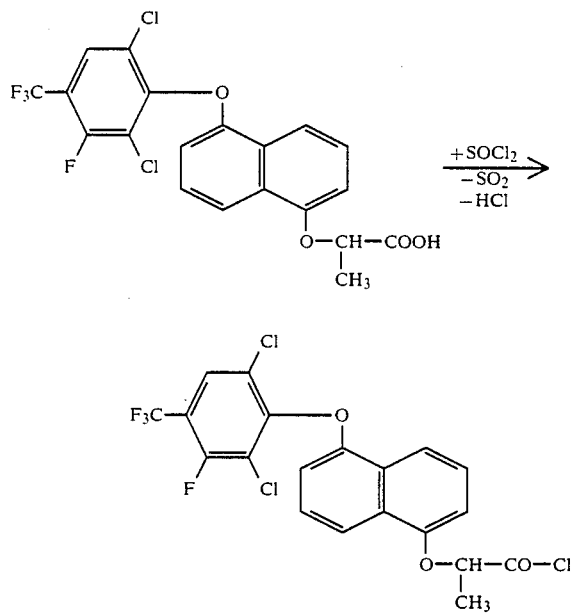

If, for example, α-(5-(2-chloro-6-fluoro-4-trifluoromethyl-phenoxy)-naphthalen-1-yl-oxy)-propionyl chloride and butanol are used as starting materials for process (e) according to the invention then the course of the reaction can be represented by the following equation:

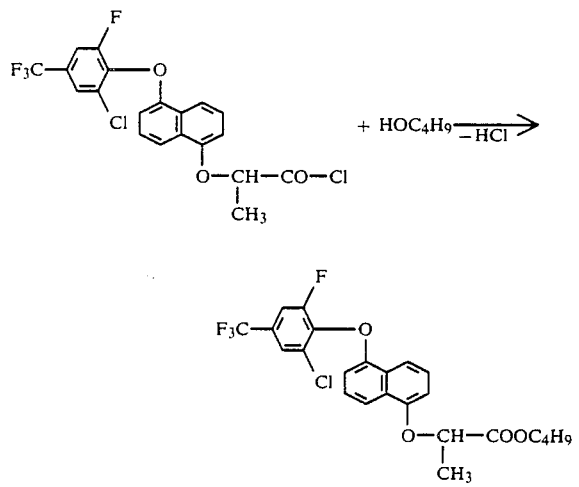

If, for example, α-(5-(2,3,6-trichloro-4-trifluoromethyl-phenoxy)-naphthalen-1-yl-oxy)-propionic acid and trimethylsilylmethyl chloride are used as starting materials for process (f) according to the invention then the course of the reaction can be represented by the following equation:

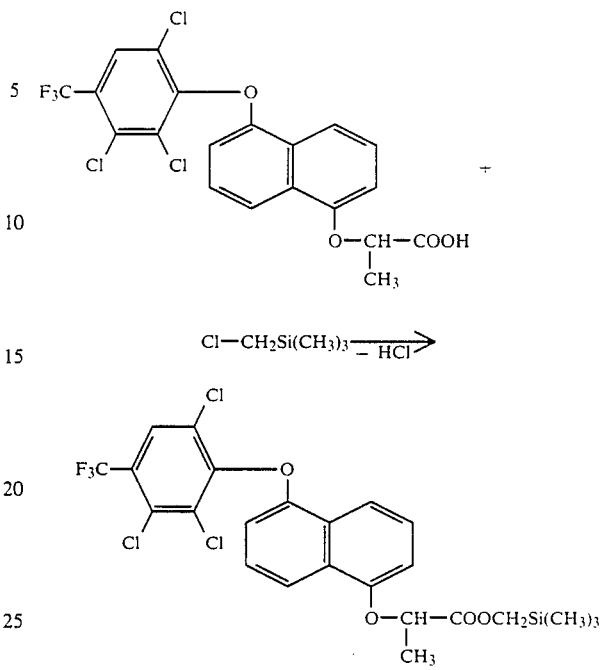

Formula (II) provides a general definition of the 5-aryloxy-1-naphthols to be used as starting materials for the preparation of compounds of the formula (I) in process (a) according to the invention.

In formula (II), $R^1$, $R^2$, $R^3$, $R^4$ and $R^5$ preferably or in particular have those meanings which have already been given above as preferable or particularly preferable for $R^1$, $R^2$, $R^3$, $R^4$ and $R^5$ in connection with the description of the compounds of the formula (I) according to the invention.

Examples of the starting materials of the formula (II) which may be mentioned are: 5-(4-trifluoromethyl-phenoxy)-1-naphthol, 5-(2-chloro-4-trifluoromethyl-phenoxy)-1-naphthol, 5-(2,6-dichloro-4-trifluoromethyl-phenoxy)-1-naphthol, 5-(2-chloro-6-fluoro-4-trifluoromethyl-phenoxy-1-naphthol, 5-(2,6-dichloro-3-fluoro-4-trifluoromethyl-phenoxy)-1-naphthol and 5-(2,3,6-trichloro-4-trifluoromethyl-phenoxy)-1-naphthol.

The starting materials of the formula (II) were hitherto unknown from the literature. The compounds of the formula (II) are obtained when corresponding halogeno-benzene derivatives of the general formula (IV)

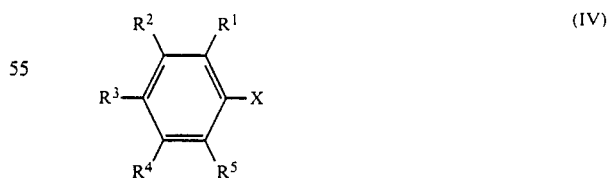

in which
$R^1$, $R^2$, $R^3$, $R^4$, $R^5$ and X have the abovementioned meanings,
are reacted with 1,5-dihydroxynaphthalene in the presence of an acid acceptor, such as, for example, sodium hydroxide or potassium hydroxide, and in the presence of a diluent, such as, for example, dimethylformamide, dimethylacetamide, dimethyl sulphoxide, tetramethylenesulphone or N-methyl-pyrrolidone, at temperatures between 20° C. and 150° C., and are worked up by customary methods.

Formula (IV) provides a general definition of the halogeno-benzene derivatives. In formula (IV), $R^1$, $R^2$, $R^3$, $R^4$ and $R^5$ preferably or in particular have those meanings which have already been given as preferable or as particularly preferable for $R^1$, $R^2$, $R^3$, $R^4$ and $R^5$ in connection with the description of the compounds of the formula (I) according to the invention, and X preferably stands for chlorine or fluorine.

Examples of the halogeno-benzene derivatives of the formula (IV) which may be mentioned are: 3-cyano-4-chloro-benzotrifluoride, 4-chloro-benzotrifluoride, 3,4-dichloro-benzotrifluoride, 3,4,5-trichloro-benzotrifluoride, 3,4-dichloro-5-fluoro-benzotrifluoride, 2,3,4,5-tetrachloro-benzotrifluoride, 3,5-dichloro-2,4-difluorobenzotrifluoride and 3-chloro-4,5-difluoro-benzotrifluoride.

The compounds of the formula (IV) are known and-/or can be prepared by processes which are known per se (compare J. Chem. Soc. 1969, 211–217; ibid. 1971, 1547–1549; EP-A 34,402; U.S. Pat. No. 4,424,396; EP-A 145,314; FR-A 2,538,380 (Chem. Abstracts 102 (1985), 61914x)).

Formula (III) provides a general definition of the propionic acid derivatives additionally to be used as starting materials in process (a) according to the invention. In formula (III), Z preferably or in particular has that meaning which has already been given above as preferable or particularly preferable in connection with the description of the compounds of the formula (I) according to the invention, and Y preferably stands for chlorine, bromine, iodine, $C_1$–$C_4$-alkylsulphonyloxy which is optionally substituted by fluorine or chlorine, or phenylsulphonyloxy which is optionally substituted by fluorine, chlorine, bromine or methyl, in particular for chlorine, bromine, methylsulphonyloxy, phenylsulphonyloxy or 4-methyl-phenylsulphonyloxy.

Examples of the compounds of the formula (III) which may be mentioned are: methyl, ethyl, propyl, isopropyl, butyl, isobutyl and sec-butyl α-chloro-, α-bromo- and α-iodo-propionates, and methyl, ethyl, propyl, butyl, isopropyl, isobutyl and sec-butyl α-methylsulphonyloxy-, α-ethylsulphonyloxy-, α-propylsulphonyloxy-, α-butylsulphonyloxy-, α-trifluoromethylsulphonyloxy-, α-phenylsulphonyloxy- and α-(4-methyl-phenylsulphonyloxy)-propionates.

The mentioned compounds of the formula (III) in each case the R isomers, the S isomers and the racemic mixtures of these isomers are taken to mean.

The starting materials of the formula (III) are known and/or can be prepared by processes which are known per se (compare DE-OS (German Published Specification) 2,758,002, DE-OS (German Published Specification) 2,854,542).

Process (a) according to the invention for the preparation of the new compounds of the formula (I) is preferably carried out using diluents. Suitable diluents in this case are practically all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone and also dimethyl sulphoxide, tetramethylenesulphone and hexamethylphosphoric triamide.

Acid acceptors which can be employed in process (a) according to the invention are all acid-binding agents conventionally utilizable for reactions of this type. Alkali metal hydroxides such as, for example, sodium hydroxide and potassium hydroxide, alkaline earth metal hydroxides such as, for example, calcium hydroxide, alkali metal carbonates and alkali metal alcoholates such as sodium carbonate and potassium carbonate, and sodium tert-butylate and potassium tert-butylate, and furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO) are preferable.

The reaction temperatures can be varied within a relatively wide range when carrying out process (a) according to the invention. In general, the process is carried out at temperatures between 0° C. and 150° C., preferably at temperatures between 20° C. and 100° C.

Process (a) according to the invention is generally carried out at atmospheric pressure. However, it is also possible to work at elevated or reduced pressure.

For carrying out process (a) according to the invention, between 0.5 and 1.2 moles, preferably between 0.7 and 1.0 mole, of propionic acid derivative of the formula (III) are generally employed per mole of 5-aryloxy-1-naphthol of the formula (II). The reaction components are generally combined at room temperature or with slight cooling and are then stirred—if desired at elevated temperature—until completion of the reaction.

Working up can be carried out in a customary manner. For example, the reaction mixture is stirred or shaken with an acid, such as, for example, hydrochloric acid or sulphuric acid and water, and also an organic solvent which is practically immiscible with water, such as, for example, methylene chloride or toluene, and the organic phase is separated off, washed with water, dried and filtered. The product of the formula (I) remaining in the residue after concentration of the filtrate can be purified in a customary manner, for example by column chromatography.

The halogeno-benzene derivatives of the formula (IV) to be used as starting materials in process (b) according to the invention have already been described above.

Formula (V) provides a general definition of the α-(5-hydroxy-naphthalen-1-yl-oxy)-propionic acid derivatives to be used furthermore as starting materials in process (b) according to the invention. In formula (V), Z preferably or in particular has that meaning which has already been given above as preferable or particularly preferable in connection with the description of the compounds of the formula (I) according to the invention.

Examples of the starting materials of the formula (V) which may be mentioned are: methyl, ethyl, propyl, isopropyl, butyl, isobutyl and sec-butyl α-(5-hydroxy-naphthalen-1-yl-oxy)-propionates.

The starting materials of the formula (V) are known and/or can be prepared by processes which are known per se (compare JP 79/32477, cited in Chem. Abstracts 91 (1979), 91510j).

Process (b) is preferably carried out using a diluent. Possible diluents are above all those which have already been mentioned in the description of process (a) according to the invention. Aprotic polar organic solvents, such as, for example, acetone, acetonitrile, methyl ethyl ketone, propionitrile, dimethylformamide, dimethylacetamide, dimethyl sulphoxide, sulpholane and N-methylpyrrolidone are particularly preferred.

Process (b) is preferably carried out in the presence of an acid acceptor. Possible acid acceptors are above all those which have already been mentioned in the description of process (a) according to the invention.

The reaction temperatures can be varied within a relatively wide range when carrying out process (b) according to the invention. In general, the process is carried out at temperatures between 0° C. and 200° C., preferably at temperatures between 20° C. and 150° C.

Process (b) according to the invention is generally carried out at atmospheric pressure. However, it is also possible to work at elevated or reduced pressure.

For carrying out process (b) according to the invention, between 0.5 and 2 moles, preferably between 0.7 and 1.5 moles, of α-(5-hydroxy-naphthalen-1-yl-oxy)-propionic acid derivative of the formula (V) are generally employed per mole of halogeno-benzene derivative of the formula (IV).

Reaction and working up can be carried out as described above for process (a).

Formula (I) provides a general definition of the compounds to be used as starting materials for carrying out process (c) according to the invention, with the proviso that Z stands for methoxy or ethoxy. In this case, the radicals $R^1$, $R^2$, $R^3$, $R^4$ and $R^5$ preferably or in particular have those meanings which have already been given above as preferable or particularly preferable in the context of the description of the compounds of the formula (I) according to the invention.

Examples of the starting materials for process (c) which may be mentioned are: methyl and ethyl α-(5-(4-trifluoromethyl)-phenoxy)-, α-(5-(2-chloro-4-trifluoromethyl-phenoxy)-, α-(5-(2,6-dichloro-4-trifluoromethyl-phenoxy)-, α-(5-(2-chloro-6-fluoro-4-trifluoromethyl-phenoxy)-, α-(5-(2,3,6-trichloro-4-trifluoromethyl-phenoxy)- and α-(5-(2,6-dichloro-3-fluoro-4-trifluoromethyl-phenoxy)-naphthalen-1-yl-oxy)-propionates.

The starting materials of the formula (I) described above for process (c) are new compounds according to the invention; they can be prepared by process (a) or (b) according to the invention.

Process (c) is carried out using alkali metal hydroxides. Examples of these which may be mentioned are lithium hydroxide, sodium hydroxide and potassium hydroxide. Sodium hydroxide is preferably used.

Process (c) is carried out in the presence of water and if appropriate in the presence of an organic solvent. Alcohols, such as, for example, methanol or ethanol are preferably employed as organic solvents.

The customary mineral acids, such as, for example, hydrochloric acid or sulphuric acid are used in process (c) for acidification.

The reaction temperatures can be varied within a relatively wide range when carrying out process (c) according to the invention. In general, the process is carried out at temperatures between 10° C. and 150° C., preferably at temperatures between 20° C. and 100° C.

Process (c) according to the invention is generally carried out at atmospheric pressure However, it is also possible to work at elevated or reduced pressure.

For carrying out process (c), between 0.1 and 10 moles, preferably between 0.5 and 2 moles, of alkali metal hydroxide are generally employed per mole of starting compound of the formula (I). The reaction components are generally combined at room temperature and the reaction mixture is stirred, at elevated temperature if desired, until the end of the reaction. The resulting crystalline reaction product can be isolated—if appropriate after concentration, cooling and acidification—by filtering with suction.

Formula (I) provides a general definition of the compounds to be used as starting materials in process (d) according to the invention, with the proviso that Z stands for hydroxyl. In this case, the radicals $R^1$, $R^2$, $R^3$, $R^4$ and $R^5$ preferably or in particular have those meanings which have already been given as preferable or particularly preferable in the context of the description of the compounds of the formula (I) according to the invention.

Examples of the starting materials for process (d) which may be mentioned are: α-(5-(4-trifluoromethyl-phenoxy)-, α-(5-(2-chloro-4-trifluoromethyl-phenoxy)-, α-(5-(2,6-dichloro-4-trifluoromethylphenoxy)-, α-(5-(2-chloro-6-fluoro-4-trifluoromethyl-phenoxy)-, α-(5-(2,3,6-trichloro-4-trifluoromethyl-phenoxy)- and α-(5-(2,6-dichloro-3-fluoro-4-trifluoromethyl-phenoxy)-naphthalen-1-yl-oxy)-propionic acid.

The starting materials of the formula (I) described above for process (d) are new compounds according to the invention; they can be prepared by process (c) according to the invention.

Process (d) is carried out using a halogenating agent. The customary agents for the conversion of carboxylic acids to carboxyl halides can be employed. Examples of these which may be mentioned are phosgene, thionyl chloride, phosphoryl chloride and benzotrichloride. Thionyl chloride is preferably used as the halogenating agent.

Process (d) is carried out in the presence of a catalyst if desired. The customary catalysts for the preparation of acid chlorides from acids, such as, for example, pyridine or dimethylformamide, can be used.

Process (d) is carried out in the presence of a diluent if desired. Inert organic solvents are from the series comprising the halogenated hydrocarbons are preferable, such as, for example, methylene chloride, chloroform, tetrachloromethane or 1,2-dichloroethane.

The reaction temperatures can be varied within a relatively wide range when carrying out process (d) according to the invention. In general, the process is carried out at temperatures between 0° C. and 100° C., preferably at temperatures between 10° C. and 90° C.

Process (d) is generally carried out at atmospheric pressure.

For carrying out process (d), between 1 and 100 moles, preferably between 2 and 50 moles, of halogenating agent are generally employed per mole of starting compound of the formula (I). The reaction components are generally combined at room temperature and the reaction mixture is stirred, if desired at elevated temperature until the end of the reaction. The reaction product remaining after removing the volatile components by distillation under reduced pressure can be purified by recrystallization, but can also be employed without further purification for further reactions.

Formula (I) provides a general definition of the compounds to be used as starting materials for process (e) according to the invention, with the proviso that Z stands for halogen. In this case, the radicals $R^1$, $R^2$, $R^3$, $R^4$ and $R^5$ preferably or in particular have those meanings which have already been given above as preferable or particularly preferable in the context of the description of the compounds of the formula (I) according to the invention and Z preferably stands for fluorine, chlorine or bromine, in particular for chlorine.

Examples of the starting materials for process (e) which may be mentioned are: α-(5-(4-trifluoromethyl-phenoxy)-, α-(5-(2-chloro-4-trifluoromethyl-phenoxy)-, α-(5-(2,6-dichloro-4-trifluoromethylphenoxy)-, α-(5-(2-chloro-6-fluoro-4-trifluoromethyl-phenoxy)-, α-(5-(2,3,6-trichloro-4-trifluoromethyl-phenoxy)- and α-(5-(2,6-dichloro-3-fluoro-4-trifluoromethyl-phenoxy)-naphthalen-1-yl-oxy)-propionyl chloride.

The starting materials of the formula (I) described above for process (e) are new compounds according to the invention; they can be prepared by process (d) according to the invention.

Formula (VI) provides a general definition of the compounds furthermore to be employed as starting materials in process (e) according to the invention. In formula (VI), Z preferably or in particular has that meaning which has already been given above as preferable or particularly preferable in connection with the description of the compounds of the formula (I) according to the invention.

Examples of the starting materials of the formula (VI) which may be mentioned are: methylamine, ethylamine, propylamine, isopropylamine, aniline, cyanamide, dimethylamine, diethylamine, hydroxylamine, o-methylhydroxylamine, hydrazine, methylsulphonylhydrazine, methanol, ethanol, propanol, isopropanol, butanol, isobutanol, sec-butanol, 2-methoxy-ethanol, 2-ethoxy-ethanol, 2-methylthio-ethanol, 2-ethylthio-ethanol, 2-benzyloxy-ethanol, 3-benzyloxy-propanol, 2-benzylthio-ethanol, diethyl and dimethyl hydroxymethane-phosphonate, dimethyl and diethyl 1-hydroxy-ethane-phosphonate, dimethyl and diethyl 1-hydroxy-1-phenyl-methanephosphonate, acetone oxime, 3-hydroxyfuran, furfuryl alcohol, perhydrofurfuryl alcohol, methyl and ethyl lactate and methyl and ethyl glycolate.

These compounds are known synthesis chemicals.

Process (e) is preferably carried out using a diluent. Possible diluents are above all those which have already been mentioned in the description of process (a) according to the invention.

Process (e) is preferably carried out in the presence of an acid acceptor. Possible acid acceptors are above all those which have already been mentioned in the description of process (a) according to the invention.

The reaction temperatures can be varied within a relatively wide range when carrying out process (e) according to the invention. In general, the process is carried out at temperatures between $-20°$ C. and $+100°$ C., preferably at temperatures between $0°$ C. and $50°$ C.

Process (e) according to the invention is generally carried out at atmospheric pressure. However, it is also possible to work at elevated or reduced pressure.

For carrying out process (e) according to the invention, the starting materials required in each case are generally employed in approximately equimolar amounts. However, it is also possible to use one of the two components employed in each case in a relatively large excess. The reactions are generally carried out in a suitable diluent in the presence of an acid acceptor and the reaction mixture is stirred for several hours at the temperature necessary in each case.

In process (e) according to the invention working up in each case takes place according to customary methods. For example, the reaction mixture is diluted—if desired after concentration—with water and the desired reaction product is extracted with an organic solvent which is practically immiscible with water, for example methylene chloride, chloroform, diethyl ether, toluene or xylene. The organic extraction solution is washed with water, dried using a customary drying agent, such as, for example, sodium sulphate, and filtered. After concentrating the filtrate, the compounds of the formula (I) are obtained as crude products which can be purified in a customary manner, for example chromatographically and/or by recrystallization.

Formula (I) provides a general definition of the compounds to be used as starting materials in process (f) according to the invention, with the proviso that Z stands for hydroxyl. In this case, the radicals $R^1$, $R^2$, $R^3$, $R^4$ and $R^5$ preferably or in particular have those meanings which have already been given above as preferable or particularly preferable in the context of the description of the compounds of the formula (I) according to the invention.

Examples of the starting materials of the formula (I) for process (f) which may be mentioned are: α-(5-(4-trifluoromethyl-phenoxy)-, α-(5-(2-chloro-4-trifluoromethyl-phenoxy)-, α-(5-(2,6-dichloro-4-trifluoromethylphenoxy)-, α-(5-(2-chloro-6-fluoro-4-trifluoromethyl-phenoxy)-, α-(5-(2,3,6-trichloro-4-trifluoromethyl-phenoxy)- and α-(5-(2,6-dichloro-3-fluoro-4-trifluoromethyl-phenoxy)-naphthalen-1-yl-oxy)-propionic acid.

The starting materials of the formula (I) described above for process (f) are new compounds according to the invention; they can be prepared by process (c) according to the invention.

Formula (VII) provides a general definition of the compounds furthermore to be employed as starting materials in process (f) according to the invention. In formula (VII), $R^6$ preferably stands for $C_1$-$C_6$-alkyl, $C_3$-$C_4$-alkenyl, $C_3$-$C_4$-alkinyl, $C_1$-$C_4$-alkoxy-$C_1$-$C_4$-alkyl, $C_1$-$C_4$-alkylthio-$C_1$-$C_4$-alkyl, phenoxy-$C_1$-$C_3$-alkyl, trimethylsilylmethyl, phenylthio-$C_1$-$C_3$-alkyl, benzyloxy-$C_1$-$C_3$-alkyl, benzylthio-$C_1$-$C_3$-alkyl or $C_1$-$C_4$-alkoxy-carbonyl-$C_1$-$C_2$-alkyl, and $X^1$ stands for chlorine, bromine or iodine.

In particular, $R^6$ in formula (VII) stands for trimethylsilylmethyl and $X^1$ stands for chlorine.

Trimethylsilylmethyl chloride is particularly preferred as the starting compound of the formula (VII) for process (f).

The starting materials of the formula (VII) are known synthesis chemicals.

Process (f) is preferably carried out using a diluent. Possible diluents are above all those which have already been mentioned in the description of process (a) according to the invention. Acetone, acetonitrile and dimethylformamide are particularly preferred.

Process (f) is preferably carried out in the presence of an acid acceptor. Possible acid acceptors are above all those which have already been mentioned in the description of process (a) according to the invention. 1,8-

Diazabicyclo-[5,4,0]-undec-7-ene (DBU) is particularly preferred.

The reaction temperatures can be varied within a relatively wide range when carrying out process (f) according to the invention. In general, the process is carried out at temperatures between 0° C. and 150° C., preferably at temperatures between 20° C. and 100° C.

Process (f) according to the invention is generally carried out at atmospheric pressure. However, it is also possible to work at elevated or reduced pressure.

For carrying out process (f), between 1 and 3 moles, preferably between 1.1 and 2.5 moles, of starting compound of the formula (VII) are generally employed per mole of starting compound of the formula (I).

Reaction and working up can be carried out as described above for process (a).

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention are particularly suitable for the selective combating of monocotyledon weeds in monocotyledon and dicotyledon cultures, above all by the post-emergence method.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention can be used as such or in the form of their formulations or alternatively as mixtures with known herbicides, finished formulations or tank mixes being possible.

Suitable components for the mixtures are known herbicides such as, for example, 1-amino-6-ethylthio-3-(2,2-dimethylpropyl)-1,3,5-triazine-2,4(1H,3H)-dione (AMETHYDIONE) or N-(2-benzthiazolyl)-N,N'-dimethyl-urea (METABENZTHIAZURON) for combating weeds in cereals; 4-amino-3-methyl-6-phenyl-1,2,4-triazin-5(4H)-one (METAMITRON) for combating weeds in sugar beets and 4-amino-6-(1,1-dimethylethyl)-3-methylthio-1,2,4-triazin-5(4H)-one (METRIBUZIN) for combating weeds in soy beans, and furthermore also 2,4-dichlorophenoxyacetic acid (2,4-D); 4-(2,4-dichlorophenoxy)-butyric acid (2,4-DB); 2,4-dichlorophenoxypropionic acid (2,4-DP); 5-(2-chloro-4-trifluoromethyl-phenoxy)-2-nitrobenzoic acid (ACIFLUORFEN); methyl 5-(2,4-dichlorophenoxy)-2-nitrobenzoate (BIFENOX); 3,5-dibromo-4-hydroxybenzonitrile (BROMOXYNIL); ethyl 2-{[(4-chloro-6-methoxy-2-pyrimidinyl)-aminocarbonyl]-aminosulphonyl}-benzoate (CHLORIMURON); 2-chloro-N-{[(4-methoxy-6-methyl-1,3,5-triazin-2-yl)-amino]carbonyl}-benzenesulphonamide (CHLORSULFURON); N,N-dimethyl-N'-(3-chloro-4-methylphenyl)-urea (CHLORTOLURON); N,N-dimethyl-N'-3-trifluoromethylphenyl)-urea (FLUOMETURON); 5-(2-chloro-4-trifluoromethyl-phenoxy)-N-methylsulphonyl-2-nitrobenzamide (FOMESAFEN); methyl 2-[4,5-dihydro-4-methyl-4-(1-methylethyl)-5-oxo-1H-imidazol-2-yl]-4(5)-methylbenzoate (IMAZAMETHABENZ); 2-[5-methyl-5-(1-methylethyl)-4-oxo-2-imidazolin-2-yl]-3-quinolinecarboxylic acid (IMAZAQUIN); 2-[4,5-dihydro-4-methyl-4-isopropyl-5-oxo-(1H)-imidazol-2-yl]-5-ethyl-pyridine-3-carboxylic acid (IMAZETHAPYR); 3,5-diiodo-4-hydroxybenzonitrile (IOXYNIL); N,N-dimethyl-N'-(4-isopropylphenyl)-urea (ISOPROTURON); (2-ethoxy-1-methyl-2-oxo-ethyl) 5-[2-chloro-4-(trifluoromethyl)-phenoxy]-2-nitrobenzoate (LACTOFEN); (2-methyl-4-chlorophenoxy)-acetic acid (MCPA); (4-chloro-2-methyl-phenoxy)-propionic acid (MCPP); N-methyl-2-(1,3-benzthiazol-2-yloxy)-acetanilide (MEFENACET); 2-{[[((4-methoxy-6-methyl-1,3,5-triazin-2-yl)-amino)-carbonyl]-amino]-sulphonyl}-benzoic acid or its methyl ester (METSULFURON); (2-chloro-4-trifluoromethylphenyl)( 3-ethoxy-4-nitro-phenyl) ether (OXYFLUORFEN); N-(1-ethylpropyl)-3,4-dimethyl-2,6-dinitroaniline (PENDIMETHALIN); methyl 3-[[[[(4-methoxy-6-methyl-1,3,5-triazin-2-yl)-amino]-carbonyl]-amino]-sulphonyl]-thiophene-2-carboxylate (THIAMETURON); 3,5,6-trichloro-2-pyridyloxyacetic acid (TRICLOPYR) and 2,6-dinitro-4-trifluoromethyl-N,N-dipropylaniline (TRIFLURALIN), and also 4-amino-6-tert.-butyl-3-ethylthio-1,2,4-triazin-5-(4H)-one (ETHIOZIN), 3-isopropyl-2,1,3-benzothiadiazin-4-one-2,2-dioxide (BENTAZON), N-phosphonomethylglycine (GLYPHOSPHATE) and O-(6-chloro-3-phenyl-pyridazin-4-yl) S-octyl thiocarbonate (PYRIDATE). Surprisingly, some mixtures also show a synergistic action.

Mixtures with other known active compounds, such as fungicides, insecticides, acaricides, nematicides, bird repellents plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1

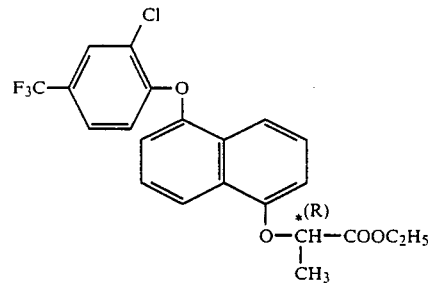

A mixture of 11.6 g (0.03 mol) of 5-(2-chloro-4-trifluoromethyl-phenoxy)-1-naphthol, 5.4 g (0.02 mol) of ethyl (S)-α-(4-methyl-phenylsulphonyloxy)-propionate, 4.2 g of potassium carbonate and 100 ml of acetonitrile is heated to boiling under reflux for 15 hours. After cooling to 20° C., the reaction mixture is acidified with 2N hydrochloric acid and shaken with toluene. The organic phase is separated off, washed with water, dried using sodium sulphate and filtered. The solvent is carefully removed from the filtrate by distillation in a waterjet vacuum. The residue is purified by column chromatography (toluene/hexane on silica gel).

1.6 g (18% of theory) of ethyl (R)-α-(5-(2-chloro-4-trifluoromethyl-phenoxy)-naphthalen-1-yl-oxy)-propionate are obtained as an oily residue of refractive index $n_d^{20} = 1.5611$.

The compounds of the formula (I)

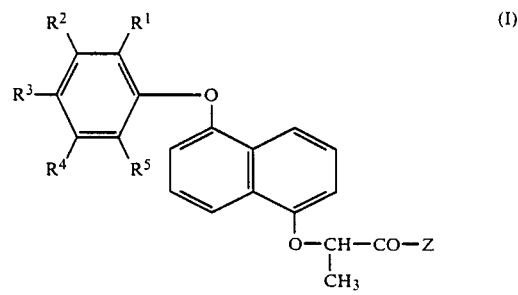

shown in Table 1 below can be obtained analogously to Example 1 and in accordance with the general description of the preparation process according to the invention.

TABLE 1

Examples of the compounds of the formula (I)

| Example No. | $R^1$ | $R^2$ | $R^3$ | $R^4$ | $R^5$ | Z | Physical data |
|---|---|---|---|---|---|---|---|
| 2 | H | H | $CF_3$ | H | H | $OC_2H_5$ | $n_D^{20} = 1.5728$ |
| 3 | Cl | H | $CF_3$ | H | Cl | $OC_2H_5$ | amorphous |
| 4 | Cl | H | $CF_3$ | H | F | $OCH_3$ | |
| 5 | Cl | Cl | $CF_3$ | H | Cl | $OC_3H_7$ | |
| 6 | Cl | F | $CF_3$ | H | Cl | $OC_4H_9$ | |
| 7 | H | H | $CF_3$ | H | H | OH | |
| 8 | Cl | H | $CF_3$ | H | H | OH | |
| 9 | Cl | H | $CF_3$ | H | F | OH | |
| 10 | Cl | Cl | $CF_3$ | H | Cl | OH | |
| 11 | Cl | F | $CF_3$ | H | Cl | OH | |
| 12 | Cl | H | $CF_3$ | H | H | Cl | |
| 13 | Cl | H | $CF_3$ | H | Cl | OH | |
| 14 | Cl | H | $CF_3$ | H | Cl | Cl | |
| 15 | Cl | Cl | $CF_3$ | H | Cl | Cl | |
| 16 | Cl | H | $CF_3$ | H | Cl | $OCH(CH_3)_2$ | |
| 17 | Cl | H | $CF_3$ | H | H | $OC_4H_9$ | |
| 18 | Cl | H | $CF_3$ | H | Cl | $OCH_2COOCH_3$ | |
| 19 | Cl | H | $CF_3$ | H | H | $OCH_2COOC_4H_9$ | |
| 20 | Cl | H | $CF_3$ | H | F | $OCH(CH_3)COOC_2H_5$ | |
| 21 | Cl | H | $CF_3$ | H | Cl | $SCH_2COOCH_3$ | |
| 22 | Cl | Cl | $CF_3$ | H | Cl | $OCH_2CH_2OCH_3$ | |
| 23 | Cl | H | $CF_3$ | H | Cl | $OCH_2CH_2SC_2H_5$ | |
| 24 | Cl | H | $CF_3$ | H | H | $OCH_2P(O)(OC_2H_5)_2$ | |
| 25 | Cl | H | $CF_3$ | H | H | $OCH(C_6H_5)P(O)(OCH_3)_2$ | |
| 26 | Cl | Cl | $CF_3$ | H | Cl | $SC_2H_5$ | |
| 27 | Cl | H | $CF_3$ | H | Cl | $NHCH(CH_3)_2$ | |
| 28 | Cl | H | $CF_3$ | H | H | $N(C_2H_5)_2$ | |
| 29 | Cl | H | $CF_3$ | H | Cl | $OCH_2CH_2OCH_2C_6H_5$ | |
| 30 | Cl | H | $CF_3$ | H | H | $OCH_2$-(2-furyl) | |
| 31 | Cl | H | $CF_3$ | H | H | $NHOCH_3$ | |
| 32 | Cl | H | $CF_3$ | H | H | $NHOC_2H_5$ | |
| 33 | Cl | H | $CF_3$ | H | Cl | $NHCH_2COOC_2H_5$ | |
| 34 | Cl | H | $CF_3$ | H | H | $NHNHSO_2CH_3$ | |
| 35 | Cl | H | $CF_3$ | H | Cl | $OCH_2Si(CH_3)_3$ | |
| 36 | CN | H | $CF_3$ | H | H | $OC_2H_5$ | (amorphous) |
| 37 | Cl | H | $CF_3$ | H | Cl | $O(CH_2)_3OCH_2C_6H_5$ | |

STARTING MATERIALS OF THE FORMULA (II)

Example (II-1)

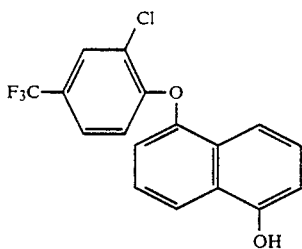

20.4 g (0.095 mol) of 3,4-dichloro-benzotrifluoride are slowly added with stirring to a mixture of 28.4 g (0.18 mol) of 1,5-dihydroxy-naphthalene, 10.1 g (0.18 mol) of potassium hydroxide powder and 100 ml of dimethyl sulphoxide, which is heated at 120° C., and the reaction mixture is stirred at 120° C. for 10 hours. After cooling to 20° C., the mixture is acidified using 2N hydrochloric acid and stirred with toleune. The crystalline product resulting, 1,5-dihydroxynaphthalene, is isolated by filtering with suction and discarded. The toluene phase is separated off and dried using sodium sulphate. After filtration, the solvent is carefully removed by distillation in vacuo.

11.6 g (36% of theoryl) of 5-(2-chloro-4-trifluoromethyl-phenoxyl)-1-naphthol are obtained as an amorphous residue ($^1$H-NMR (CDCl$_3$), δ (R$^2$): 7.73 ppm, when R$^1$=Cl, R$^3$=CF$_3$).

The starting materials of the formula (II) shown in Table 2 below can be prepared analogously to Example (II-1).

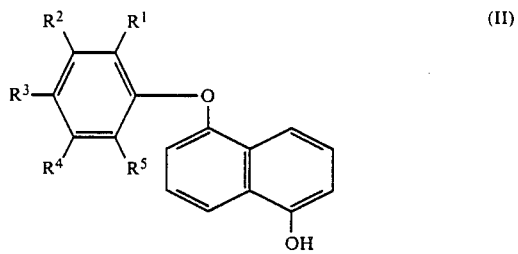

(II)

TABLE 2

| Examples of the starting materials of the formula (II) | | | | | |
|---|---|---|---|---|---|
| Example No. | R$^1$ | R$^2$ | R$^3$ | R$^4$ | R$^5$ |
| II-2 | H | H | CF$_3$ | H | H |
| II-3 | Cl | H | CF$_3$ | H | Cl |
| II-4 | Cl | Cl | CF$_3$ | H | Cl |
| II-5 | Cl | F | CF$_3$ | H | Cl |
| II-6 | Cl | H | CF$_3$ | H | F |
| II-7 | CN | H | CF$_3$ | H | H |

USE EXAMPLES

The compound shown below is referred to as the comparison substance in the following use examples:

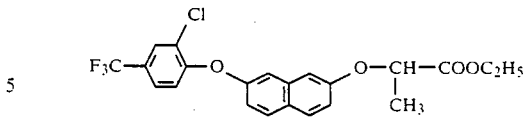

Ethyl α-(7-(2-chloro-4-trifluoromethyl-phenoxy)-naphthalen-2-yl-oxy)-propionate (known from EP-A 179,015/Example 1).

Example A

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test the compound according to preparation Example (1), for example, shows, together with good selectivity in soy beans, cotton and wheat, considerably stronger action against problem weeds, such as, for example, Digitaria, Panicum and Setaria, than the comparison substance (A).

It will be appreciated that the instant specification and claims are set forth by way of illustration and not limitation, and that various modifications and changes may be made without departing from the spirit and scope of the present invention.

What is claimed is:

1. An α-(5-aryloxy-naphthalen-1-yl-oxy)-propionic acid derivative of the formula

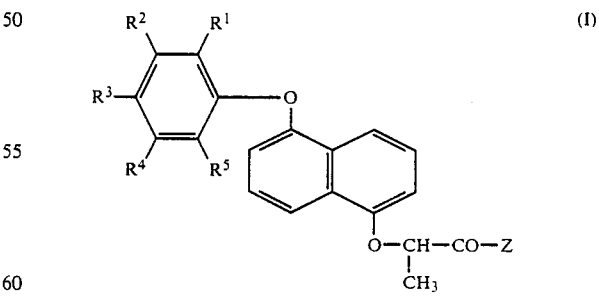

in which
R$^1$ stands for hydrogen, halogen, cyano or trifluoromethyl,
R$^2$ stands for hydrogen or halogen,
R$^3$ stands for halogen, cyano, trifluoromethyl or trifluoromethoxy,
R$^4$ stands for hydrogen or halogen, R⁵ stands for hydrogen or halogen and Z stands for halogen, hydroxyl, or for the —O—R⁶ group, wherein R⁶ stands for an optionally halogen-substituted radical from the series comprising alkyl, alkenyl, alkinyl, alkoxyalkyl, or aralkyl.

2. An α-5-(aryloxy-naphthalen-1-yl-oxy)-propionic acid derivative according to claim 1, in which R¹ stands for hydrogen, fluorine, chlorine, bromine, cyano or trifluoromethyl, R² stands for hydrogen, fluorine or chlorine, R³ stands for fluorine, chlorine, bromine, cyano, trifluoromethyl or trifluoromethoxy, R⁴ stands for hydrogen, fluorine or chlorine, R⁵ stands for hydrogen, fluorine, chlorine or bromine and Z stands for chlorine, hydroxyl, group, wherein R⁶ stands for a radical from the group consisting of $C_1$-$C_6$-alkyl, $C_3$-$C_4$-alkenyl, $C_3$-$C_4$-alkinyl, $C_1$-$C_4$-alkoxy-$C_1$-$C_4$-alkyl, and benzyl.

3. An α-(5-aryloxy-naphthalen-1-yl-oxy)-propionic acid derivative according to claim 1, in which R¹ stands for hydrogen, cyano, fluorine or chlorine, R² stands for hydrogen, fluorine or chlorine, R³ stands for trifluoromethyl, R⁴ stands for hydrogen, fluorine or chlorine, R⁵ stands for hydrogen, fluorine or chlorine and Z stands for chlorine, hydroxyl, or for the —O—R⁶ group, wherein R⁶ stands for $C_1$-$C_2$-alkyl-$C_1$-$C_2$-alkoxy-$C_1$-$C_2$-alkyl, and benzyl.

4. A substantially pure R enantiomer of a compound according to claim 3.

5. A compound according to claim 1, wherein such compound is ethyl (R)-α-(5-(2-chloro-4-trifluoromethylphenoxy)-naphthalen-1-yl-oxy)-propionate of the formula 6. A herbicidal composition comprising a herbicidally effective amount of a compound according to claim 1 and a diluent.

7. A method of combating unwanted vegetation which comprises applying to such vegetation or to a locus from which it is desired to exclude such vegetation a herbicidally effective amount of a compound according to claim 1.

8. A method of combating unwanted vegetation which comprises applying to such vegetation or to a locus from which it is desired to exclude such vegetation a herbicidally effective amount of a compound according to claim 5.

9. A 5-aryloxy-1-naphthol of the formula in which

R¹ stands for hydrogen, halogen, cyano or trifluoromethyl,

R² stands for hydrogen, or halogen,

R³ stands for halogen, cyano, trifluoromethyl or trifluoromethoxy,

R⁴ stands for hydrogen or halogen, and

R⁵ stands for hydrogen or halogen.

10. A compound according to claim 1, wherein such compound is ethyl (5-(4-trifluoromethyl-phenoxy)-naphthalen-1-yl-oxy)-propionate of the formula 11. A method of combating unwanted vegetation which comprises applying to such vegetation or to a locus from which it is desired to exclude such vegetation a herbicidally effective amount of a compound according to claim 10.

* * * * *

UNITED STATES PATENT AND TRADEMARK OFFICE
CERTIFICATE OF CORRECTION

PATENT NO. : 4,994,601

DATED : February 19, 1991

INVENTOR(S) : Haug et al.

It is certified that error appears in the above-identified patent and that said Letters Patent is hereby corrected as shown below:

Col. 23, line 7    After " alkoxyalkyl, " insert -- aryloxyalkyl, --

Col. 23, line 19   Before " group " insert -- of for the $-O-R^6$ --

Co. 23, line 35    Delete "$C_1-C_2$-alkyl" (1st occurrence) and substitute -- $C_1-C_4$-alkyl--.

Col. 23, line 36   Delete " and " and substitute -- or --

Signed and Sealed this

Twenty-seventh Day of April, 1993

Attest:

MICHAEL K. KIRK

Attesting Officer    Acting Commissioner of Patents and Trademarks